(12) United States Patent
Krass

(10) Patent No.: US 6,896,656 B2
(45) Date of Patent: May 24, 2005

(54) NEUROLOGICAL TESTING APPARATUS

(76) Inventor: Alvin Krass, 162 Alderbrook Rd., Little Silver, NJ (US) 07739

(*) Notice: Subject to any disclaimer, the term of this patent is extended or adjusted under 35 U.S.C. 154(b) by 32 days.

(21) Appl. No.: 10/293,367

(22) Filed: Nov. 14, 2002

(65) Prior Publication Data
US 2003/0055322 A1 Mar. 20, 2003

Related U.S. Application Data

(63) Continuation of application No. 09/678,104, filed on Oct. 4, 2000, now Pat. No. 6,517,480.

(51) Int. Cl.[7] .................................................. A61B 5/00
(52) U.S. Cl. ..................... 600/300; 600/595; 128/904
(58) Field of Search .................... 600/300–301, 600/587–595, 558, 559, 544–545, 28; 128/898, 904, 920, 897; 434/236–238; 607/45

(56) References Cited

U.S. PATENT DOCUMENTS

| | | |
|---|---|---|
| 4,166,452 A | 9/1979 | Generales, Jr. |
| 4,276,546 A | 6/1981 | Krass |
| 4,854,329 A | 8/1989 | Walruff |
| 5,595,488 A | 1/1997 | Gozlan et al. |
| 5,807,114 A | 9/1998 | Hodges et al. |
| 5,904,639 A | 5/1999 | Smyser et al. |
| 5,911,581 A | 6/1999 | Reynolds et al. |
| 5,995,868 A | 11/1999 | Dorfmeister et al. |
| 6,007,459 A | 12/1999 | Burgess |
| 6,097,981 A | 8/2000 | Freer |
| 6,280,198 B1 * | 8/2001 | Calhoun et al. ............ 434/236 |

FOREIGN PATENT DOCUMENTS

EP      0 251 541      1/1988

OTHER PUBLICATIONS www.brain.com/promotions/bcn/, Introducing the Cognitive Care System, pp. 1–2, Searched on Sep. 13, 2000.
*Psychological Assessment Resources, Inc.*, Kaufman WISC–111® Integrated Interpretive System, p. 57, Jan. 1999.
*The Psychological Corporation, The Catalog for Psychological and Intervention Products*, MicroCog™: Assessment of Cognitive Functioning, p. 72, 2000.

* cited by examiner

*Primary Examiner*—Max F. Hindenburg
*Assistant Examiner*—Michael Astorino
(74) *Attorney, Agent, or Firm*—Westerman, Hattori, Daniels & Adrian LLP

(57) ABSTRACT

An apparatus for performing neuropsychological tests on a patient includes a microprocessing unit adapted for carrying out test procedures which is connected to an interface to a sensory signal generating device comprising at least one of a visual information display, an indication light, and a sound generator, an interface to a reaction detecting device comprising at least one of a dynamometer, a knob, and a touch screen, and an interface to a memory for reading test procedures stored in the memory. At least one test procedure comprising instructions for the generation of sensory signals and the detection of a patient reaction is stored in the memory and is performed by generating the sensory signals on the sensory generating device and by detecting a patient's reaction through the reaction detecting device.

25 Claims, 2 Drawing Sheets

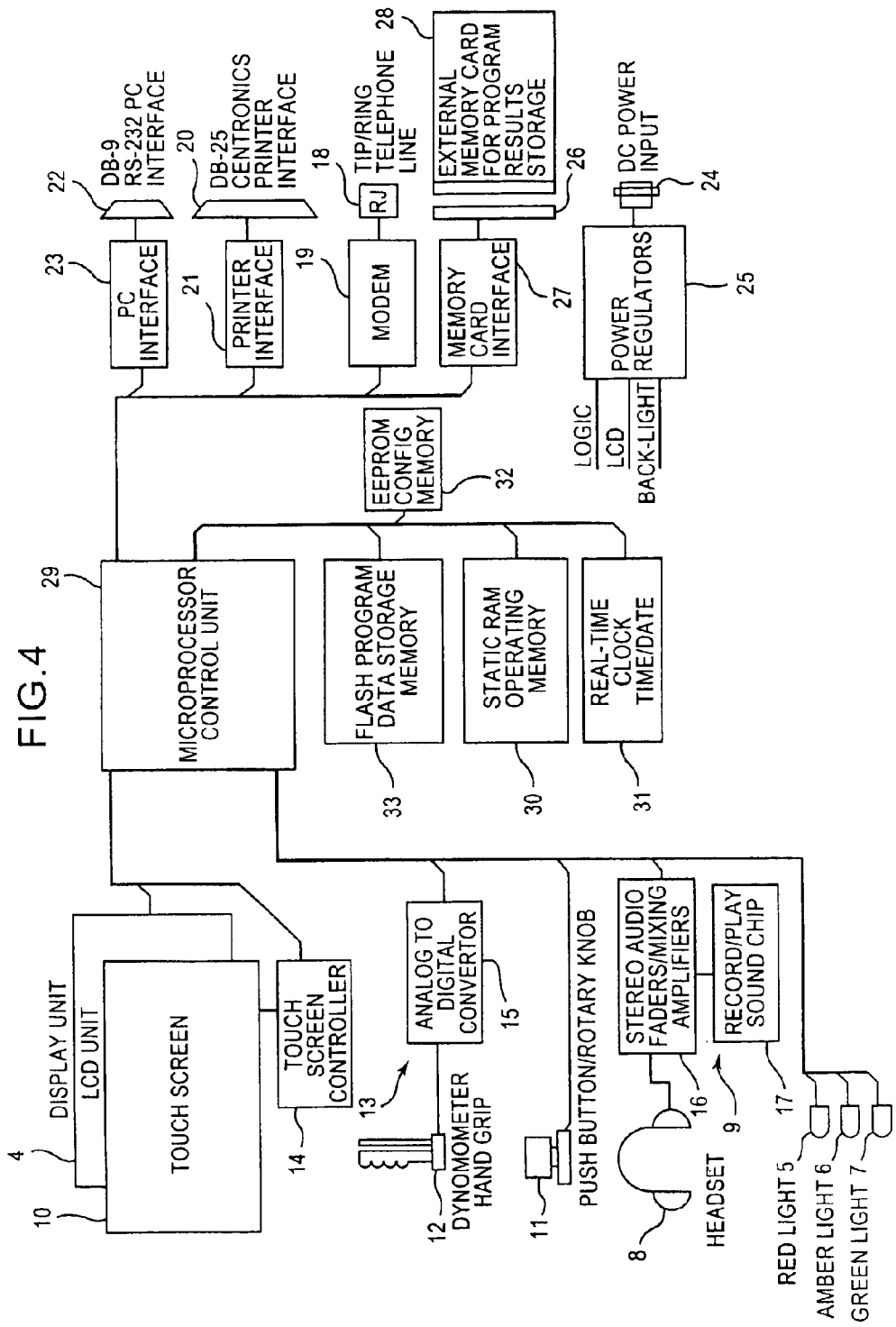

NEUROLOGICAL TESTING APPARATUS

This application is a continuation of prior application Ser. No. 09/678,104 filed Oct. 4, 2000, now U.S. Pat. No. 6,517,480, which is hereby incorporated by reference.

FIELD OF THE INVENTION

The present invention concerns an apparatus for measuring neuro-cognitive activity by carrying out neuropsychological tests, in particular for testing impairments and competencies relating to neuropsychological function.

DESCRIPTION OF THE PRIOR ART

Neuropsychological tests are used by doctors to measure underlying perceptual, cognitive, and information processing abilities, and in particular, assess deficits or changes in attention, immediate and short term memory, visual-perceptual functions, sequencing functions, logical problem solving, calculation skills, reaction time, simultaneous information processing abilities, and executive functioning. Apparatuses are known which measure only a few patient functions such as reaction time. However, in the known apparatuses, other patient functions are not tested, so that only a very narrow and imprecise assessment of the patient's abilities is possible based on this type of tests.

SUMMARY OF THE INVENTION

A purpose of the present invention is to provide an apparatus for carrying out neuropsychological tests which enables assessment of a wide variety of neurocognitive areas.

Accordingly, in a first aspect of the present invention, an apparatus for performing neuropsychological tests on a patient comprises:

means for generating a plurality of sensory signals comprising visual signals, auditory signals, or both visual and auditory signals; and means for detecting physical movement of a patient in response to said generated plurality of sensory signals.

Advantageously, the plurality of sensory signals is determined prior to performing a test on a patient. Visual signals and auditory signals may be simultaneously generated. The apparatus may further comprise one or several additional means such as means for storing, processing, or both storing and processing information obtained from the means for detecting physical movement, means for reporting on the information obtained from the means for detecting physical movement, and means for selecting the plurality of sensory signals prior to performing a test on a patient.

In another aspect of the present invention, an apparatus for performing neuropsychological tests on a patient comprises a microprocessing unit adapted for carrying out test procedures, said microprocessing unit being connected to:

an interface to a sensory signal generating device comprising at least one of a visual information display, an indication light, and a sound generator;

an interface to a reaction detecting device comprising at least one of a dynamometer, a knob, and a touch screen; and an interface to a memory for reading test procedures stored in the memory, wherein at least one test procedure comprising instructions for the generation of sensory signals and the detection of a patient reaction is stored in the memory and is performed by generating the sensory signals on the sensory generating device and by detecting a patient's reaction through the reaction detecting device.

Advantageously, the memory is an internal memory of the apparatus. In the alternative, the memory may be a card or a set of cards, in which case the apparatus may comprise a card reading device for insertion and reading of the card or cards. In another embodiment, the interface to a memory is an interface to a computer or a network of computers which comprise the memory.

Advantageously, the microprocessor is connected to an interface to a reporting device for reporting information on reactions detected through the reaction detecting device. This interface to a reporting device may be to a printer, or to a computer or a network of computers, or both.

The sensory signal generating device may comprise one or several among a sound generator which may be a headset, one or a plurality of indication lights which may be of different colors. The reaction detecting device may comprise one or several among a dynamometer which may be a hand grip, a knob which may be a push button, a rotary switch, or a combination push button and rotary switch. Specifically, the sensory signal generating device advantageously comprises an information display device, an indication light, and a sound generator, and the reaction detecting device advantageously comprises a touch screen, a dynamometer and a knob.

In an embodiment of the apparatus of the present invention, a plurality of sensory signals are generated simultaneously, and in particular, visual and audio signals may be generated simultaneously. Also, a plurality of physical reactions of the patient are advantageously detected during the performance of the test procedure.

An advantage of the apparatus of the present invention is that a much more extensive evaluation of neurocognitive areas of patients can be obtained than with currently known apparatuses. For example, it may be possible to evaluate impairments in neurocognitive areas using one or several of the following measures:

Response to multi-sensory stimuli

Ability to perform a repetitive motor task with and without outside auditory or visual distraction Grip strength, persistence and side variability Cognitive perceptual competence and memory Performance in tracking through a series of increasingly complex patterns These assessments may be used to identify who may be suffering from such disorders as senile dementia, Alzheimer's disease, attention deficit disorder, post-traumatic cognitive and neurological disabilities, impairment in perceptual-motor function reflecting an inability to perform motor tasks such as driving, and/or other activities requiring effective motor performance.

Another advantage of the apparatus of the present invention is that it may be possible to carry out a wide variety of neuropsychological tests using a single unitary, compact, and portable instrument which is very easy to use.

BRIEF DESCRIPTION OF DRAWINGS

FIG. 4 is a block diagram of the apparatus of FIG. 1.

DETAILED DESCRIPTION OF THE INVENTION

Figure 1:
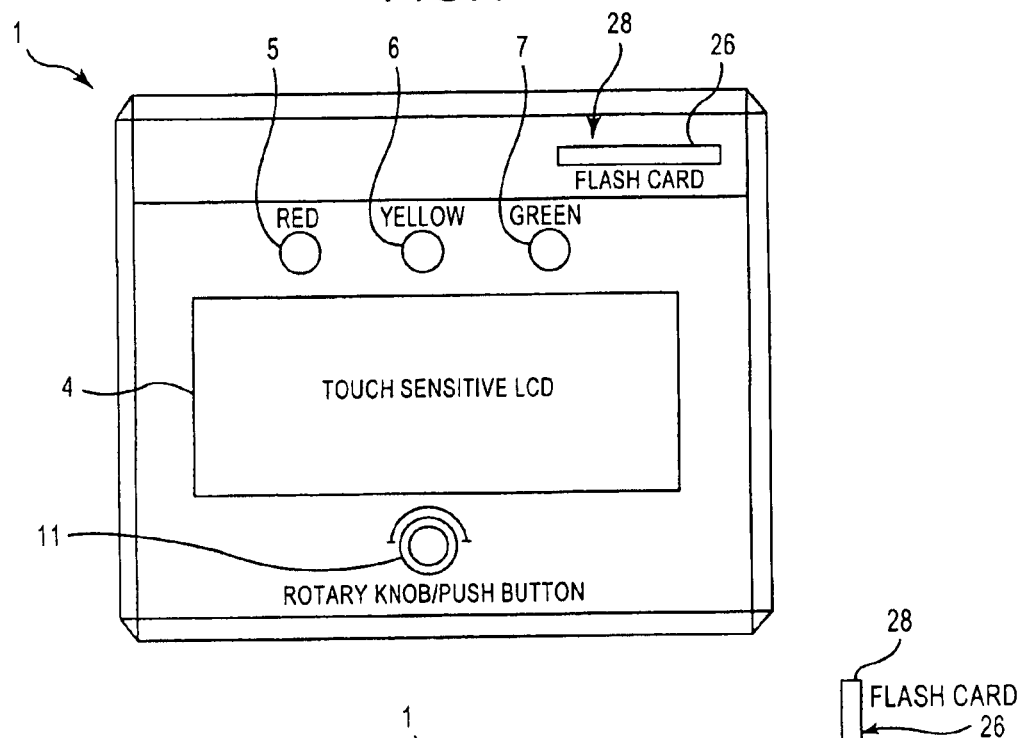
FIG. 1 is a top view of an embodiment of an apparatus according to the present invention.
Figure 2:
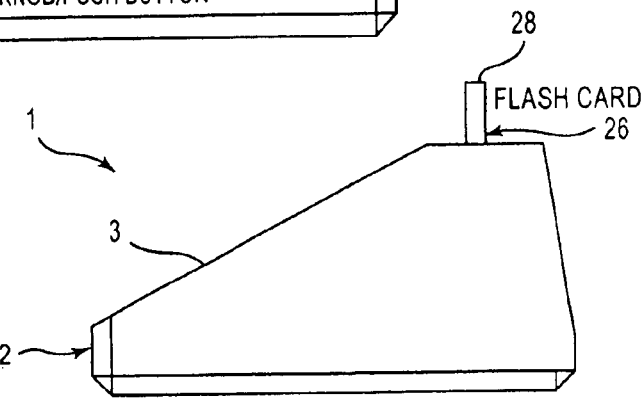
FIG. 2 is a lateral view of the apparatus of FIG. 1.

The example of apparatus according to the present invention which is shown in FIG. 1 comprises a casing 1 having a generally rectangular block shape except that a front face 2 comprises a slanted portion 3. Visual signal generating means in the form of a LCD screen 4 and lights 5, 6 and 7 are located on the front face. Audio signal generating means in the form of a headset 8 is connected to an audio interface 9 on the front face of the apparatus. Reaction detecting means is present in the form of a touch screen 10 and a knob 11 located on the front face and a dynamometer 12 connected to a dynamometer interface 13.

In this embodiment, as shown in FIG. 4, the LCD screen 4 is associated to the touch screen 10 to form a display unit which functions both as display means to display information on the display unit and as reaction detecting means to detect actions by a user on the touch screen. The touch screen 10 is connected to a touch screen controller 14.

The knob 11 is adapted to detect tapping by a finger. For example, the knob may be a simple switch which is movable between off and on positions by pushing. In that case, only the on or off position of the knob is detected. In this embodiment, the knob is rotatable around a central axis. In that case, both the on or off position and the angular position of the knob are detected.

The dynamometer 12 is a hand grip which is connected to the interface 13 comprising an analog/digital converter 15. The hand grip comprises a handle portion and is adapted to detect the grip strength of a patient. Specifically, the grip handle comprises two mutually connected handle portions which are movable between a first position away from each other and a second position close to each other, and resilient means (not shown) such as a spring which tends to force the handle portions away from each other. The relative position of the two handle portions is detected electronically so as to provide an information on the grip strength. Optionally, the grip may also comprise a switch button. Examples of such grips are known and used in particular in electronic games. In an alternative embodiment, the hand grip could be mounted on the casing. In that case, the hand grip could be a foldable grip.

Advantageously, various grips adapted for measuring different gripping strengths can be successively mounted on the machine, such as a grip for children and a grip for adults. Also, the apparatus may comprises several different or similar grips.

As shown on FIG. 4, the headset 8 is connected to the interface 9 which comprises stereo audio faders and mixing amplifiers 16 and a record/play sound chip 17. The sound generator thus constituted can generate true, sampled sounds which may be prerecorded and preloaded into the apparatus, or may be modified as part of the modification of a test procedure.

Figure 3:
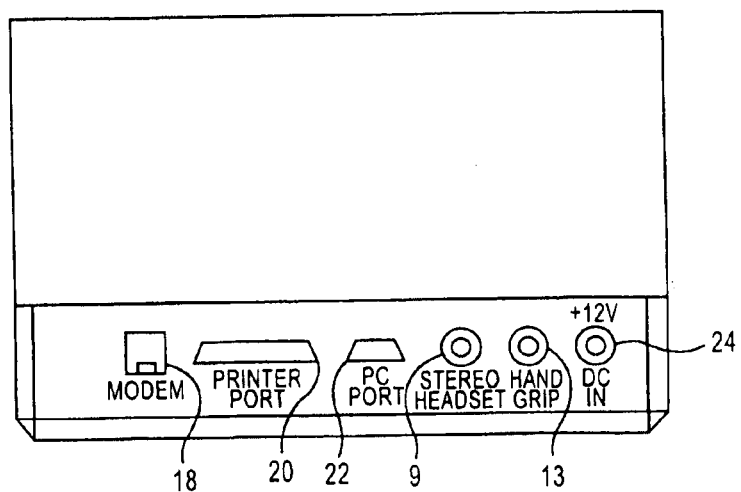
FIG. 3 is a back view of the apparatus of FIG. 1.

As shown on FIGS. 3 and 4, the apparatus also comprises an interface port 18 associated with a modem 19 for connection to a network of computers for communication and modifications of test procedures, test results, or both, an interface port 20 associated with a printer interface 21 for connection to a printer for printing test procedures, test results, or both, an interface port 22 associated with a PC interface 23 for connection to a personal computer for communication and modifications of test procedures, test results, or both, and an interface port 24 associated with a power regulator 25 for connection to a source of electrical current. In addition, a separate interface port for connection to a network could be provided.

Further, the apparatus comprises a memory card interface port 26 associated with a memory card interface 27, which are adapted to receive and connect to external memory cards such as memory card 28 for storing test procedures, test results, or both.

As shown on FIG. 4, inside the casing is disposed a central processing unit (CPU) 29 which is adapted to sequentially perform the test functions, including executing memorized or detected instructions and processing corresponding information. The CPU is connected electronically to each of the visual and audio display means so as to provide appropriate display signals to these display means, to the reaction detecting means so as to detect, collect and process information on the patient's reactions, and to the interface ports. The CPU is also connected to static RAM operating memory 30 and real-time clock 31 for providing time and date, as well as an EEPROM 32 for storing user configuration and modifications, and a flash program data storage memory 33 for storing test procedure files received from an external source, such as a computer or a network of computers, as well as test results.

The CPU thus controls means for generating sensory signals adapted to be displayed on the sensory signal generating means, and means for detecting, analyzing and processing detection signals adapted for detecting, analyzing and processing signals generated by the reaction detecting means.

During a test, the CPU executes instructions by controlling the generation of sensory information directed to the patient, such as visual information or auditory information on the sensory display means, and detecting, analyzing and processing information on the patient's reaction from the reaction detecting means.

Specifically, the apparatus shown in FIGS. 1–4 functions as follows. The apparatus is adapted to administer to a patient a series of neurological tests designed to measure neuro-cognitive functions. More particularly, tests are designed to identify whether or not an individual is impaired in one of a series of activities which are characteristically identified as reflecting impairment or adequacy of performance in areas of neuro-cognitive activity. Tests may be administered alone or in sequence of several tests. In a sequence, tests may be administered in any order. The test instructions and the test sequence is preferably prerecorded in the memory of the apparatus or in a card. However, a choice between several test sequences, or a choice between individual tests in a test sequence, may be available, for example by displaying visual prompts on the screen and detecting a user's response on the touch screen. Also, the test sequences may be selected or modified from a remote location, such as from a computer.

When the apparatus is connected to a power source, the screen lights up and a visual indication is displayed on the screen requesting a user to enter personal data such as name, address, age, and then, press a start icon on the touch screen to start testing. When the patient touches the touch screen, a corresponding signal is received by the CPU and the test or the sequence of tests is started. The patient is then directed to follow directions on display on the screen or audio instructions communicated through the headset. Each test performed, either alone or in a sequence, may be selected from the following tests, or from other tests also made available in the apparatus. In the following, examples of tests which can be performed on the apparatus are described.

A first test is adapted to measure abstract reasoning ability and visual memory. A number of shapes forming a first pattern are shown on the screen for a fixed period of time. The screen is then cleared and a comparative pattern comprising the same number of shapes is flashed on the screen.

The patient is asked to identify whether the comparative pattern is the same or different as the pattern shown previously. For example, the shapes are triangles, each having a pointer indicated by a blocked point of each triangle in a specific series of directions. The patient is thus called upon to recognize whether the pattern of directional pointers is the same or different. A portion of the screen is reserved for gathering the patient's reaction. Thus, a question is displayed on the screen, with a "yes" portion and a "no" portion, and the patient's response is detected by detecting whether the patient presses the corresponding portion of the touch screen.

Next, an increased number of shapes forming a second pattern is displayed on the screen for a second fixed period of time which may be the same as the length of the previous pattern or different. For example, the new pattern can comprise four triangles instead of three, each triangle also with pointers in specific directions. The pattern is then cleared, a second comparative pattern is shown on the screen, and the patient's reaction is detected.

A succession of such procedures is performed and the patient's reactions are detected. The number of such procedures, the length of time of display, the presentation of the patterns and the comparative patterns are pre-programmed in the apparatus, or the apparatus is adapted for programming these features prior to carrying out the test, for example through prompts on the touch screen.

A second test is adapted to measure a patient's ability to change directions with a visual symbol acted out in a motor activity, i.e., to measure visual motor perceptual accuracy of performance and response time for performing a basic motor task. A first maze design is displayed on the screen and the patient is asked to trace with the finger through the maze on the touch screen. The time for performing this task and the number of errors are detected. This sequence is repeated with a second maze, a third maze, etc., which become more and more complex.

A third test is adapted to measure the ability to track a moving target. A visual target which moves randomly in the transverse direction of the screen is displayed on the screen, and the patient is asked to align a pointer with the target by rotating the knob to the right or to the left. The shape, trajectory and speed of the target may be fixed or may vary during the test.

A fourth test is adapted to measure consistency of effort level and hand grip strength on the right and left side. A visual or audio squeeze signal is displayed, and the patient is asked to squeeze the grip when the squeeze signal is displayed. The grip strength is detected. The number and the type of squeeze signals may vary during the test. For example, the patient may be asked to squeeze with the left or right hand, a given number of time, for a given length of time, with a given strength, etc.

A fifth test is adapted to measure finger tapping. This test is used to measure neuro-cognitive and neuropsychological deficiencies. A visual or audio tapping signal is displayed, and the patient is asked to tap the knob for a given length of time. For example, a visual instruction is displayed on the screen, a start and stop sounds are displayed through the headset, and the timing and number of taps are detected. The detected information can be processed by the CPU, for example by comparing the test results with pre-recorded standard normal performances.

A sixth test is adapted to measure the ability to follow directions of a simple visually directed motor skill task. A first pattern of shapes is displayed on the screen, and the patient is asked to press the knob successively to have the shapes disappear one after the other. Then, a second pattern, a third pattern, etc., are displayed, and the patient's action on the knob is detected.

A seventh test is adapted to measure physical response to a visual or auditory stimulus. A visual signal such as a simple drawing is displayed on the screen, and the patient is asked to press the knob as soon as the drawing is seen. In the alternative, an audio signal such as a beeping sound is given through the headset, and the patient is asked to press the knob as soon as the signal is heard. The patient's action on the knob and the time delay between the signal and the action on the knob are detected. For example, the drawing is a simple line, or consists of a series of words or letters. The audio signal is given to the left ear, the right ear, or both ears. The number of trials and the type of signals can vary during the test.

In each of the tests, an additional factor can be incorporated in that visual and/or auditory distraction can be presented to the patient. For example, distracting patterns can be displayed on the screen, or distracting sounds can be performed in the headset, or both.

For each of the tests, the test procedures are pre-programmed in the apparatus, or the test procedures can be modified by a user either directly from the touch screen or by changing cards, or through an external computer or network of computers. The tests can be adapted to particular objectives or uses. For examples, individual features of each test, such as the type of visual or audio signals and the type of patient's action which is detected, can be modified. Also, individual features of the above tests can be combined to form new tests. The test procedures described above are given only as examples, and other test procedures may be used in addition or in place of these examples.

In alternative embodiments of the present invention, the apparatus associates other combinations among the components of the sensory signal generating means and reaction detecting means which have been described in connection with FIGS. 1–4, or comprise additional components. Any of such components is mounted on the apparatus or may be connected to the apparatus through a wire connection or other communication device.

What is claimed is:

1. Apparatus for performing neuropsychological tests on a patient, comprising:
   means for generating a plurality of sensory signals comprising visual signals, auditory signals, or both visual and auditory signals;
   means for determining perceptual-motor function in a neuropsychological test by detecting physical movement of a patient in response to said generated plurality of sensory signals, said detected physical movement comprising at least one of (i) the trajectory or speed of a rotating motion of a rotary knob turned by the patient and (ii) the accuracy of a path traced by the patient on a touch screen; and
   means for reporting information on the detected physical movement of the patient through an interface to a computer or network of computers, or both.

2. Apparatus according to claim 1, wherein the plurality of sensory signals is determined prior to performing a test on a patient.

3. Apparatus according to claim 1, wherein visual signals and auditory signals are simultaneously generated.

4. Apparatus according to claim 1, further comprising means for storing, processing, or both storing and processing information obtained from the means for detecting physical movement.

5. Apparatus according to claim 1, wherein said detected physical movement comprises the trajectory or speed of a rotating motion of the rotary knob turned by the patient.

6. Apparatus according to claim 1, wherein said detected physical movement comprises the accuracy of a path traced by the patient on the touch screen.

7. The apparatus of claim 1, wherein the information is reported through a network of computers.

8. The apparatus of claim 7, wherein the information is reported through a modem.

9. The apparatus of claim 1, wherein the test procedure is selected or modified from a remote location.

10. Apparatus for performing neuropsychological tests on a patient, comprising a microprocessing unit adapted for carrying out test procedures, said microprocessing unit being connected to an interface to a sensory signal generating device comprising at least one of a visual information display, an indication light, and a sound generator;

an interface to a reaction detecting device for determining perceptual-motor function in a neuropsychological test, said reaction detecting device comprising at least one of (i) a rotary knob that measures the trajectory or speed of a rotating motion of the rotary knob turned by the patient and (ii) a touch screen that measures the accuracy of a path traced by the touch screen; and an interface to a memory for reading test procedures stored in the memory, wherein at least one test procedure comprising instructions for the generation of sensory signals and the detection of a patient reaction is stored in the memory and is performed by generating the sensory signals on the sensory generating device and by detecting a patient's reaction through the reaction detecting device, and and interface to a computer or network of computers, or both, wherein information on reactions of the patient detected through the reaction detecting device is reported to the computer or network of computers or both.

11. Apparatus according to claim 10, wherein the memory is an internal memory of the apparatus.

12. The apparatus of claim 10, wherein the reaction detecting device comprises the rotary knob adapted to detect the trajectory or speed of a rotating motion when turned by the patient.

13. The apparatus of claim 10, wherein the reaction detecting device comprises the touch screen adapted to detect the accuracy of a path traced by the patient.

14. The apparatus of claim 10, wherein the sensory signal generating device comprises an information display device, an indication light, and a sound generator.

15. The apparatus of claim 10, wherein the reaction detecting device comprises the touch screen, the rotary knob, and a dynamometer.

16. The apparatus of claim 10, wherein the information is reported through a network of computers.

17. The apparatus of claim 9, wherein the information is reported through a modem.

18. The apparatus of claim 10, wherein the test procedure is selected or modified from a remote location.

19. A process for performing neuropsychological tests on a patient, comprising:

generating a plurality of sensory signals comparing visual signals, auditory signals, or both visual and auditory signals;

determining perceptual-motor function in a neuropsychological test by detecting physical movement of a patient in response to said generated plurality of sensory signals, said detected physical movement of a patient in response to said generated plurality of sensory signals, said detected physical movement comprising at least one of (i) the trajectory or speed of a rotating motion of a rotary knob turned by the patient and (ii) the accuracy of a path traced y the patient on a touch screen; and reporting information on the detected physical movement of the patient through an interface to a computer or network of computers, or both.

20. Process according to claim 19, further comprising assessing the reported information to identify whether the patient is suffering from at least one disorder selected from senile dementia, Alzheimer's disease, attention deficit disorder, post-traumatic cognitive and neurological disabilities, impairment in perceptual-motor function.

21. Process according to claim 20, comprising assessing the reported information to identify whether the patient is suffering from Alzheimer's disease.

22. Process according to claim 20, comprising assessing the reported information to identify whether the patient is unable to drive.

23. A process for performing neuropsychological tests on a patient, comprising:

generating a plurality of sensory signals comparing visual signals, auditory signals, or both visual and auditory signals;

determining perceptual-motor function in a neuropsychological test by detecting physical movement of a patient in response to said generated plurality of sensory signals, said detected physical movement of a patient in response to said generated plurality of sensory signals, said detected physical movement comprising at least one of (i) the trajectory or speed of a rotating motion of a rotary knob turned by the patient and (ii) the accuracy of a path traced y the patient on a touch screen; and reporting information on the detected physical movement of the patient through an interface; and assessing the reported information to identify whether the patient is suffering from at least one disorder selected from senile dementia, Alzheimer's disease, attention deficit disorder, post-traumatic cognitive and neurological disabilities, impairment in perceptual-motor function.

24. Process according to claim 23, comprising assessing the reported information to identify whether the patent is suffering from Alzheimer's disease.

25. Process according to claim 23, comprising assessing the reported information to identify whether the patient is unable to drive.

* * * * *